United States Patent

Hamamura et al.

[11] Patent Number: 5,565,586
[45] Date of Patent: Oct. 15, 1996

[54] OXIDATIVE PROCESS FOR THE PREPARATION OF ALLYL QUINONE DERIVATIVES

[75] Inventors: Kimio Hamamura, Chiba Prefecture; Chiaki Seki, Aichi Prefecture; Masayuki Konishi, Ibaraki Prefecture, all of Japan

[73] Assignee: Eisai Chemical Co., Ltd., Japan

[21] Appl. No.: 396,777

[22] Filed: Mar. 1, 1995

[30] Foreign Application Priority Data

Mar. 2, 1994 [JP] Japan .................................. 6-054835
Dec. 2, 1994 [JP] Japan .................................. 6-299637

[51] Int. Cl.$^6$ ............................................. C07C 50/02
[52] U.S. Cl. ................................................. 552/310
[58] Field of Search ........................................ 552/310

[56] References Cited

U.S. PATENT DOCUMENTS 4,139,545  2/1979  Morimoto et al. ................. 552/310
4,526,719  7/1985  Terao et al. ........................ 552/310

*Primary Examiner*—Rebecca Cook
*Attorney, Agent, or Firm*—Wenderoth, Lind & Ponack

[57] ABSTRACT

A process for the industrial preparation of the quinone derivative represented by the following general formula:

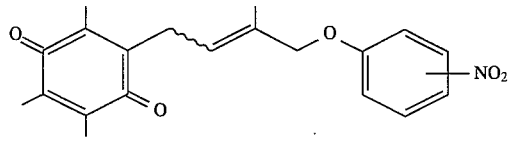

which is an intermediate for chroman derivatives useful as a blood sugar lowering agent, and novel intermediates, encompasses the following:

(1) Oxidation of the corresponding hydroquinone derivative, and (2) Hydrolysis of the corresponding acyl hydroquinone derivative with a Claisen alkali, followed by the oxidation of resulting hydrolyzate.

2 Claims, No Drawings

OXIDATIVE PROCESS FOR THE PREPARATION OF ALLYL QUINONE DERIVATIVES

BACKGROUND OF THE INVENTION a) Field of the Invention

The present invention relates to a process for the industrial preparation of quinone derivatives such as for example 2-[4'-(p-nitrophenoxy)-3'-methyl-2'-butenyl]-3,5,6 -trimethyl-1,4-benzoquinone, and novel intermediates.

There are many useful chroman derivatives, as pharmaceuticals, including at first 5-[{4-[3,4-dihydro-6-hydroxy-2,5,7,8 -tetramethyl-2H-1-benzopyrane-2-yl)methoxy]phenyl}methyl]-2,4-thiazolidinedion (Code Name: CS-045, GAS Registry No.97322-87-7) which is a blood suger lowering agent. For the preparation of these chroman derivatives, there are generally used, as intermediate, 2-[4'-(p-nitrophenoxy)-3'-methyl-2'-butenyl]-3,5,6 -trimethyl-1,4-benzoquinone.

b) Description of the Related Art

Conventionally, EP-543,346, for example, discloses the preparation of 2-[4'-(p-nitrophenoxy)-3'-methyl-2'-butenyl] -3,5,6 -trimethyl-1,4-benzoquinone (XII) which comprises condensing 3,5,6-trimethyl-1,4-hydroxyquinone (VIII) and 1-chloro-2-methyl- 3-butene-2-ol (IX) in accordance with a Friedel-Crafts reaction, then oxidizing the resulting condensate (X), and followed by adding p-nitrophenol to the oxidized condensate (XI). This preparation process will be described, as follows, where X means a halogen atom.

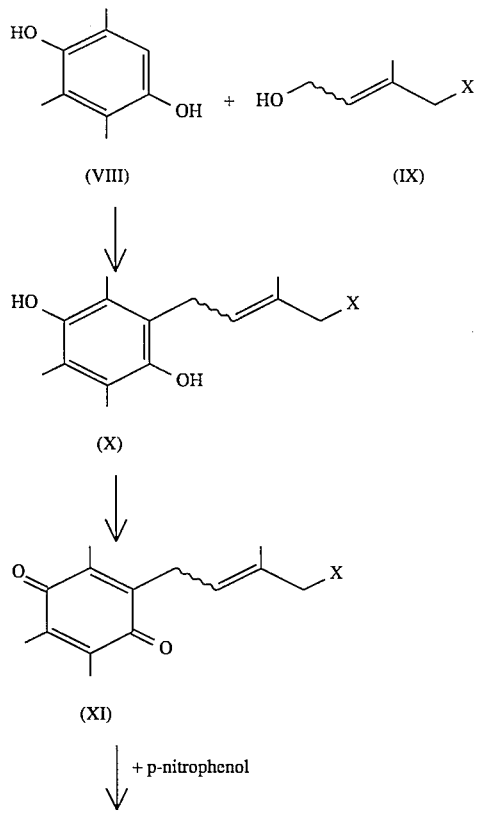

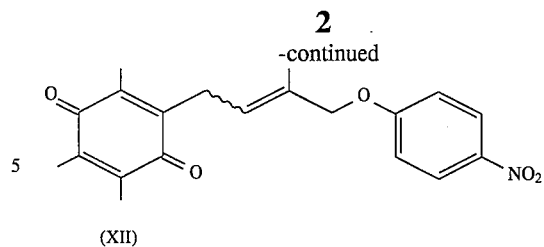

According to the process described in EP-543,346, 3,5,6-trimethyl-1,4-hydroquinone (VIII) and an allyl halide such as 1-chloro-2-methyl-2-butene-3-ol (IX) are utilized. However, since such an allyl halide has a very high reactivity, it will produce many decomposites and other structural isomers, and it is therefore difficult to purify the object compound. Furthermore, the allyl halide is unstable and hence, it must be prepared in situ, with some problems in the operationally safe point of view, for instance, its stimulation and the like.

2-(1-Chloro-2-methyl-2-butene-4-yl)-3,5,6-trimethyl-1,4-hydroquinone (X) obtained in accordance with the Friedel-Crafts condensation and 2-(1-chloro-2-methyl-2-butene-4-yl)- 3,5,6-trimethyl-1,4-quinone (XI) obtained by oxidizing said hydroquinone (X) are also unstable. Accordingly, they will produce many decomposites and by-products in their respective reaction steps, and it is therefore difficult to purify the object compound, with a lower yield accompanied therewith. Namely, it can not be concluded that this process of the prior art is an industrially proper process.

As mentioned above, there has not been an industrially excellent preparation process capable of preparing 2-[4' -(p-nitrophenoxy)-3'-methyl-2'-butenyl]-3,5,6-trimethyl-1, 4-benzoquinone (XII) useful as pharmaceutical intermediates, at a high yield and with safety.

SUMMARY OF THE INVENTION

An object of the present invention is therefore to provide an industrially excellent process for the preparation of the quinone derivatives (II) represented by the following general formula:

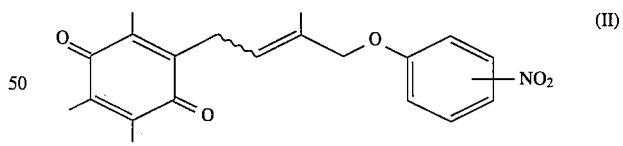

such as 2-[4'-(p-nitrophenoxy)-3'-methyl-2'-butenyl]-3,5,6-trimethyl- 1,4-benzoquinone (XII) which is useful as a pharmaceutical intermediate, and novel preparation intermediates.

The present inventors have been studying hard for improving the drawbacks of the aforementioned process of the prior art. As a result, the inventors have found that the quinone derivatives (II), including at first 2-[4'-(p-nitrophenoxy)-3'-methyl-2'-butenyl]-3,5,6-trimethyl-1,4-benzoquinone (XII), can be industrially prepared at a high yield and with safety in accordance with the undermentioned processes, and have completed this invention. Namely, the present invention encompasses the undermentioned processes:

(1) Oxidation of a hydroquinone derivative (I) represented by the following general formula:

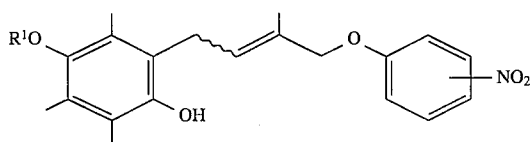

wherein $R^1$ means a hydrogen atom, an aliphatic acyl group or aromatic acyl group; and (2) Hydrolysis of an acyl hydroquinone derivative (III) represented by the following general formula:

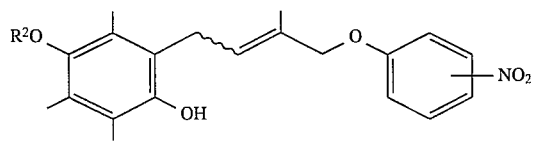

wherein $R^2$ means an aliphatic acyl group or aromatic acyl group with Claisen alkali, followed by oxidation of the resulting hydrolyzate (III') represented by the following general formula:

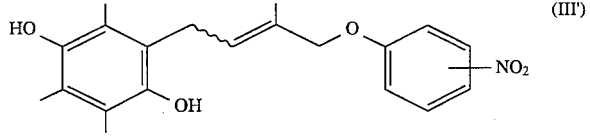

The following represents schematic view of the chemical reaction equations of the process for the preparation of the aforementioned quinone derivatives (II) according to the present invention. In the formulae, $R^1$ means a hydrogen atom, an aliphatic acyl group or aromatic acyl group, and $R^2$ means an aliphatic acyl group or aromatic acyl group.

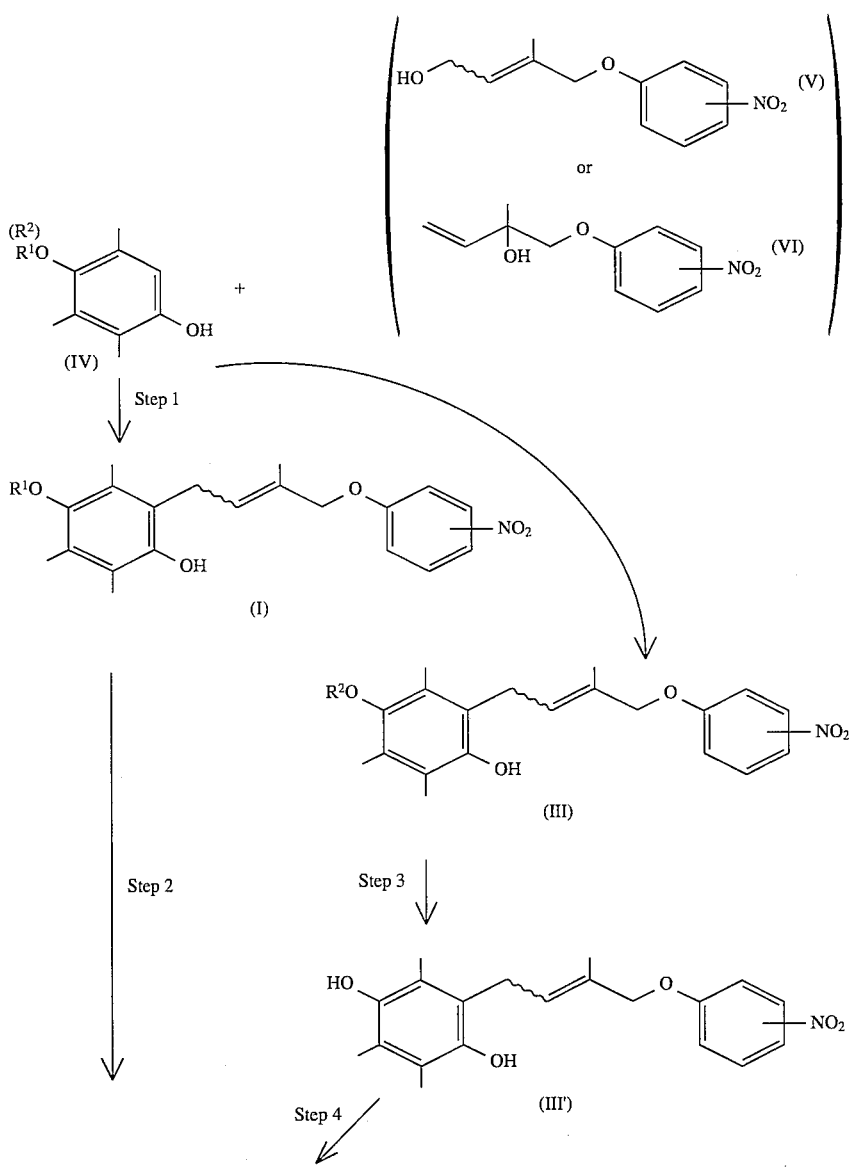

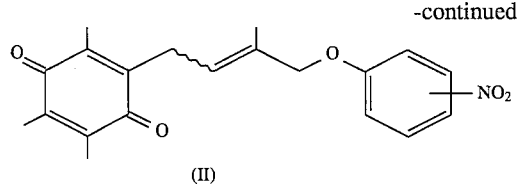

(II)

The hydroquinone derivatives (I) which are starting feed materials in the present invention are novel substances, and they are prepared by reacting a trimethyl hydroquinone derivative (IV) with a primary allyl alcohol derivative (V) or tertiary allyl alcohol derivative (VI).

The primary allyl alcohol derivatives (V) or tertiary allyl alcohol derivatives (VI) are also novel compounds, and they can be prepared, for instance, in accordance with the chemical reaction equation is described below. In the formulae, L means an eliminable group in an organic synthesis reaction, and Ac means an acetyl group.

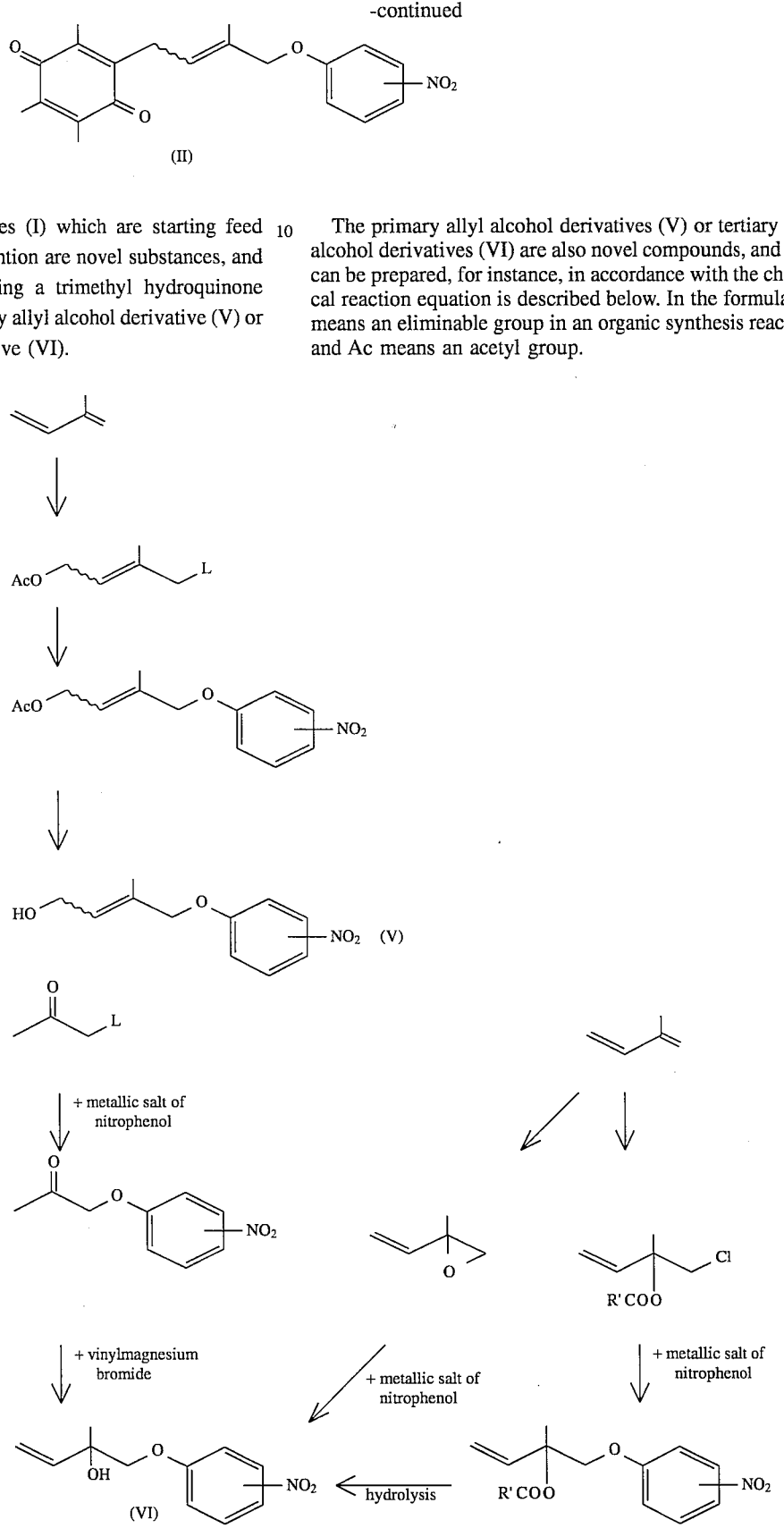

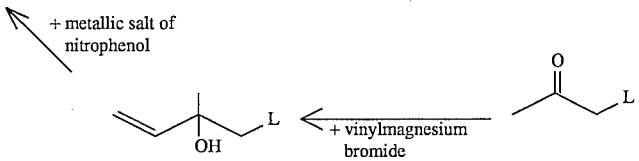

DETAILED DESCRIPTION OF THE INVENTION AND PREFERRED EMBODIMENTS

The hydroquinone derivatives (I) according to the present invention are novel compounds and they will be represented by the following formula (I):

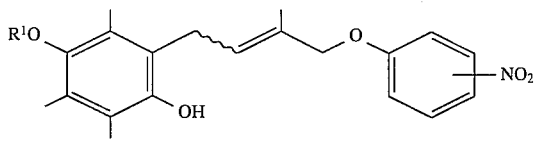

wherein $R^1$ means a hydrogen atom, an aliphatic acyl group or aromatic acyl group.

The aliphatic acyl group in the present invention means a group derived from straight chain or branched chain lower aliphatic carboxylic acids such as a formyl group, acetyl group, propionyl group, butyryl group or valeryl group, and the like.

The aromatic acyl group therein means a group derived from aromatic carboxylic acids such as a benzoyl group, toluoyl group or xyloyl group which may be substituted.

The hydroquinone derivatives (I) have double bonds in their molecule, resulting in the provision of their geometrical isomers of both the cis (Z) and trans (E) forms. However, they are equivalently used of course, without limiting thereto in the present invention. Further, the substitutional position of the nitro group thereof may include, but is not limited to, the o-, m- and p-positions.

Further practically as the hydroquinone derivatives (I), for example, the following compounds can be exemplified, but the hydroquinone derivatives (I) in the present invention are not limited thereto.

(1) 2-[4'-(p-Nitrophenoxy)-3'-methyl-2'-butenyl]-3,5,6 -trimethyl-1,4-hydroquinone,
(2) {2-[4'-(p-Nitrophenoxy)-3'-methyl-2'-butenyl]-3,5,6 -trimethyl-1,4-hydroquinone-4-yl}formate,
(3) {2-[4'-(p-Nitrophenoxy)-3'-methyl-2'-butenyl]-3,5,6 -trimethyl-1,4-hydroquinone-4-yl}acetate,
(4) {2-[4'-(p-Nitrophenoxy)-3'-methyl-2'-butenyl]-3,5,6 -trimethyl-1,4g-hydroquinone-4-yl}propionate,
(5) {2-[4'-(p-Nitrophenoxy)-3'-methyl-2'-butenyl]-3,5,6 trimethyl-1,4-hydroquinone-4-yl}butyrate,
(6) {2-[4'-(p-Nitrophenoxy)-3'-methyl-2'-butenyl]-3,5,6 -trimethyl-1,4-hydroquinone-4-yl}valerate,
(7) {2-[4'-(p-Nitrophenoxy)-3'-methyl-2'-butenyl]-3,5,6 -trimethyl-1,4-hydroquinone-2-yl}benzoate,
(8) {2-[2'-(p-Nitrophenoxy)-3'-methyl-2'-butenyl]-3,5,6-trimethyl-1,4-hydroquinone-4-yl}chlorobenzoate,
(9) {2-[4'-(p-Nitrophenoxy)-3'-methyl-2'-butenyl]-3,5,6 -trimethyl-1,4-hydroquinone-4-yl}methoxybenzoate,
(10) {2-[2'-(p-Nitrophenoxy)-3'-methyl-2'-butenyl]-3,5,6-trimethyl-1,4-hydroquinone-2-yl}nitrobenzoate, and
(11) {2-[4'-(p-Nitrophenoxy)-3'-methyl-2'-butenyl]-3,5,6-trimethyl-1,4-hydroquinone-4-yl}toluylate.

The hydroquinone derivatives (I) are novel compounds, and they are useful as a preparation intermediate (a starting material) of 2-[4'-(p-nitrophenoxy)-3'-methyl-2'-butenyl]-3,5,6-trimethyl-1,2- benzoquinone (XII) which is a preparation intermediate of the chroman derivatives useful as pharmaceuticals, including at first 5-[{2-[3,2-dihydro-6-hydroxy-2,5,7,8 -tetramethyl-2H-1-benzopyrane-2-yl)methoxy]phenyl}methyl]-2,4-thiazolidinedion (Code Name: CS-045, CAS Registry No.97322-87-7).

The quinone derivatives (II) will be represented by the following formula. The quinone derivatives (II) also have double bonds in their molecule, resulting in the existence of their geometrical isomers of the cis (Z) and trans (E) forms. However, they are both used of course, without not limiting thereto in the present invention. Also the substitutional position of the nitro group thereof may include, but is not limited to, the o-, m- and p-positions.

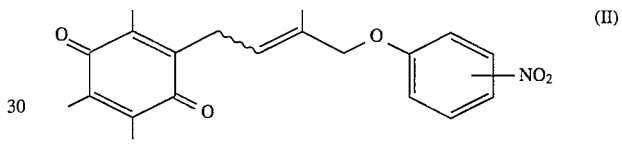

Further concretely as the quinone derivatives (II), the following compounds can be exemplified.

(1) (2'E)-2-[4'-(p-Nitrophenoxy)-3'-methyl-2'-butenyl]- 3,5,6-trimethyl-1,4-benzoquinone,
(2) (2'Z)-2-[4'-(p-Nitrophenoxy)-3'-methyl-2'-butenyl]- 3,5,6-trimethyl-1,4-benzoquinone,
(3) (2'E)-2-[4'-(m-Nitrophenoxy)-3'-methyl-2'-butenyl]- 3,5,6-trimethyl-1,4-benzoquinone,
(4) (2'Z)-2-[4'-(m-Nitrophenoxy)-3'-methyl-2'-butenyl]- 3,5,6-trimethyl-1,4-benzoquinone,
(5) (2'E)-2-[4'-(o-Nitrophenoxy)-3'-methyl-2'-butenyl]- 3,5,6-trimethyl-1,4-benzoquinone, and
(6) (2'Z)-2-[4'-(o-Nitrophenoxy)-3'-methyl-2'-butenyl]- 3,5,6-trimethyl-1,4-benzoquinone.

The acyl hydroquinone derivatives (III) will be represented by the following general formula:

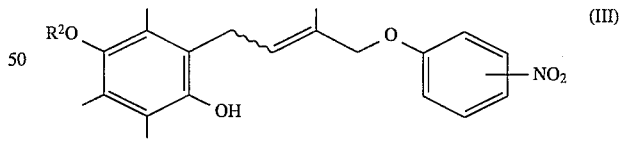

wherein $R^2$ means an aliphatic acyl group or aromatic acyl group. As concrete examples of the aliphatic acyl groups and aromatic acyl groups here, the same examples as in the aforementioned $R^1$ can be exemplified. The acyl hydroquinone derivatives (III) also have double bonds in their molecule, resulting in the provision of their geometrical isomers of the cis (Z) and trans (E) forms, but they are not limited thereto in the present invention. Furthermore, the substitutional position of the nitro group thereof may include, but is not limited to the o-, m- and p-positions.

As the acyl hydroquinone derivatives (III), for example, the following compounds can be further concretely exemplified, but the acyl hydroquinone derivatives (III) in the present invention are not limited thereto.

(1) {2-[4'-(p-Nitrophenoxy)-3'-methyl-2'-butenyl]-3,5,6-trimethyl-1,4-hydroquinone-4-yl}formate,
(2) {2-[4'-(p-Nitrophenoxy)-3'-methyl-2'-butenyl]-3,5,6-trimethyl-1,4-hydroquinone-4-yl}acetate,
(3) 2-[4'-(p-Nitrophenoxy)-3'-methyl-2'-butenyl]-3,5,6-trimethyl-1,4-hydroquinone-4-yl}propionate,
(4) 2-[4'-(p-Nitrophenoxy)-3'-methyl-2'-butenyl]-3,5,6-trimethyl-1,4-hydroquinone-4-yl}butyrate,
(5) 2-[4'-(p-Nitrophenoxy)-3'-methyl-2'-butenyl]-3,5,6-trimethyl-1,4-hydroquinone-4-yl}valerate,
(6) 2-[4'-(p-Nitrophenoxy)-3'-methyl-2'-butenyl]-3,5,6-trimethyl-1,4-hydroquinone-4-yl}benzoate,
(7) 2-[4'-(p-Nitrophenoxy)-3'-methyl-2'-butenyl]-3,5,6-trimethyl-1,4-hydroquinone-4-yl}chlorobenzoate,
(8) 2-[4'-(p-Nitrophenoxy)-3'-methyl-2'-butenyl]-3,5,6-trimethyl-1,4-hydroquinone-4-yl}methoxybenzoate,
(9) {[2-[4'-(p-Nitrophenoxy)-3'-methyl-2'-butenyl]-3,5,6-trimethyl-1,4-hydroquinone-4-yl}nitrobenzoate, and
(10) 2-[4'-(p-Nitrophenoxy)-3'-methyl-2'-butenyl]-3,5,6-trimethyl-1,4-hydroquinone-4-yl}toluylate.

The trimethyl hydroquinone derivatives (IV) will be represented by the following general formula:

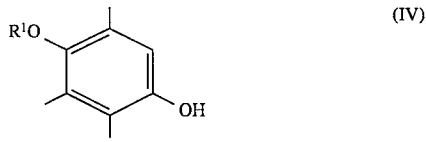
(IV)

wherein $R^1$ has the same meaning as defined above. As the trimethyl hydroquinone derivatives (IV); for example, the following compounds can be further concretely exemplified, but the trimethyl hydroquinone derivatives (IV) in the present invention are not limited thereto.
(1) 2,3,5-Trimethyl-1,4-hydroquinone,
(2) 1-O-Formyl-2,3,5-trimethyl-1,4-hydroquinone,
(3) 1-O-Acetyl-2,3,5-trimethyl-1,4-hydroquinone,
(4) -O-Propionyl-2,3,5-trimethyl-1,4-hydroquinone,
(5) 1-O-Butyryl-2,3,5-trimethyl-1,4-hydroquinone,
(6) 1-O-Valeryl-2,3,5-trimethyl-1,4-hydroquinone,
(7) 1-O-Benzoyl-2,3,5-trimethyl-1,4-hydroquinone,
(8) 1-O-Chlorobenzoyl-2,3,5-trimethyl-1,4-hydroquinone,
(9) 1-O-Nitrobenzoyl-2,3,5-trimethyl-1,4-hydroquinone,
(10) 1-O-Anisoyl-2,3,5-trimethyl-1,4-hydroquinone,
(11) 1-O-Toluoyl-2,3,5-trimethyl-1,4-hydroquinone, and
(12) 1-O-Xyloyl-2,3,5-trimethyl-1,4-hydroquinone.

The primary allyl alcohol derivatives (V) will be represented by the following general formula:

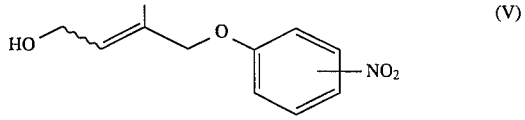
(V)

As the primary allyl alcohol derivatives (V), for example, the following compounds can be further concretely exemplified.
(1) 4-(p-Nitrophenoxy)-3-methyl-2-butene-1-ol,
(2) 4-(m-Nitrophenoxy)-3-methyl-2-butene-1-ol, and
(3) 4-(o-Nitrophenoxy)-3-methyl-2-butene-1-ol.

The tertiary allyl alcohol derivatives (VI) will be represented by the following general formula:

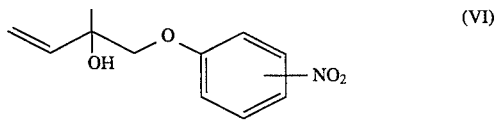
(VI)

As the tertiary allyl alcohol derivatives (VI), for example, the following compounds can be further concretely exemplified.
(1) 1-(p-Nitrophenoxy)-2-methyl-3-butene-2-ol,
(2) 1-(m-Nitrophenoxy)-2-methyl-3-butene-2-ol, and
(3) 1-(o-Nitrophenoxy)-2-methyl-3-butene-2-ol.

Finally, alkenyl ether derivatives (VII) according to the present invention are novel compounds represented by the following general formula, and they are useful as a starting material for preparing the hydroquinone derivatives (I).

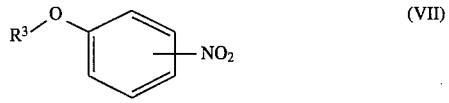
(VII)

where $R^3$ means a group represented by the following general formula:

wherein $R^4$ means a hydrogen atom, an aliphatic acyl group or aromatic acyl group, or means a group represented by the following general formula:

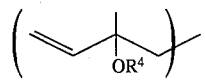

wherein $R^4$ has the same as defined above. As concrete examples of the aliphatic acyl groups and aromatic acyl groups in $R^4$ here, the same examples as in the aforementioned $R^1$ can be exemplified. The alkenyl ether derivatives (VII) also have double bonds in their molecule, resulting in the provision of their geometrical isomers of the cis (Z) and trans (E) forms, but they are not limited thereto in the present invention. Furthermore, the substitutional position of the nitro group thereof may include, but is not limited to the o-, m- and p-positions.

As the alkenyl ether derivatives (VII), for example, the following compounds can be further concretely exemplified, but the alkenyl ether derivatives (VII) in the present invention are not limited thereto.
(1) 4-(p-Nitrophenoxy)-3-methyl-2-butene-1-ol,
(2) [4-(p-Nitrophenoxy)-3-methyl-2-butenyl]formate,
(3) [4-(p-Nitrophenoxy)-3-methyl-2-butenyl]acetate,
(4) [4-(p-Nitrophenoxy)-3-methyl-2-butenyl]propionate,
(5) [4-(p-Nitrophenoxy)-3-methyl-2-butenyl]butyrate,
(6) [4-(p-Nitrophenoxy)-3-methyl-2-butenyl]valerate,
(7) [4-(p-Nitrophenoxy)-3-methyl-2-butenyl]benzoate,
(8) [4-(p-Nitrophenoxy)-3-methyl-2-butenyl]chlorobenzoate,
(9) [4-(p-Nitrophenoxy)-3-methyl-2-butenyl]methoxybenzoate,
(10) [4-(p-Nitrophenoxy)-3-methyl-2-butenyl]nitrobenzoate,
(11) [4-(p-Nitrophenoxy)-3-methyl-2-butenyl]toluylate,
(12) 1-(p-Nitrophenoxy)-2-methyl-3-butene-2-ol,
(13) [1-(p-Nitrophenoxy)-2-methyl-3-butene-2-yl]formate,
(14) [1-(p-Nitrophenoxy)-2-methyl-3-butene-2-yl]acetate,
(15) [1-(m-Nitrophenoxy)-2-methyl-3-butene-2-yl]formate,
(16) [1-(m-Nitrophenoxy)-2-methyl-3-butene-2-yl]acetate,
(17) [1-(o-Nitrophenoxy)-2-methyl-3-butene-2-yl]formate, and
(18) [1-(o-Nitrophenoxy)-2-methyl-3-butene-2-yl]acetate.

The alkenyl ether derivatives (VII) according to the present invention are novel substances, and they can be prepared by anyone of the following processes.

(1) Nitrophenol and a reactive ester such as (4-bromo-3-methyl-2-butenyl) acetate are condensed in the presence of a base to prepare an ester of the primary allyl alcohol derivative (V), and said ester is then hydrolyzed at need to prepare the primary allyl alcohol derivative (V);

(2) Nitrophenoxy acetone is reacted with vinylmagnesium bromide to prepare the tertiary allyl alcohol derivative (VI), (3) 1-Chloro-2-methyl-3-butene-2-ol or the like derived from chloroacetone is reacted with nitrophenol to prepare the tertiary allyl alcohol derivative (VI), (4) 2-Ethenyl-2-methyloxirane (CAB Resistry No. 1838-94-4) derived from isoprene is reacted with a metallic salt of nitrophenol to prepare the tertiary allyl alcohol derivative (VI), and (5) (1-Chloro-2-methyl-3-butene-2-yl) acetate derived from isoprene and nitrophenol are reacted with each other to prepare an ester of the tertiary allyl alcohol derivative (VI), and said ester is then hydrolyzed at need to prepare the tertiary allyl alcohol derivative (VI).

Namely, these processes for preparing the alkenyl ether derivatives (VII) are represented by the following chemical reaction scheme.

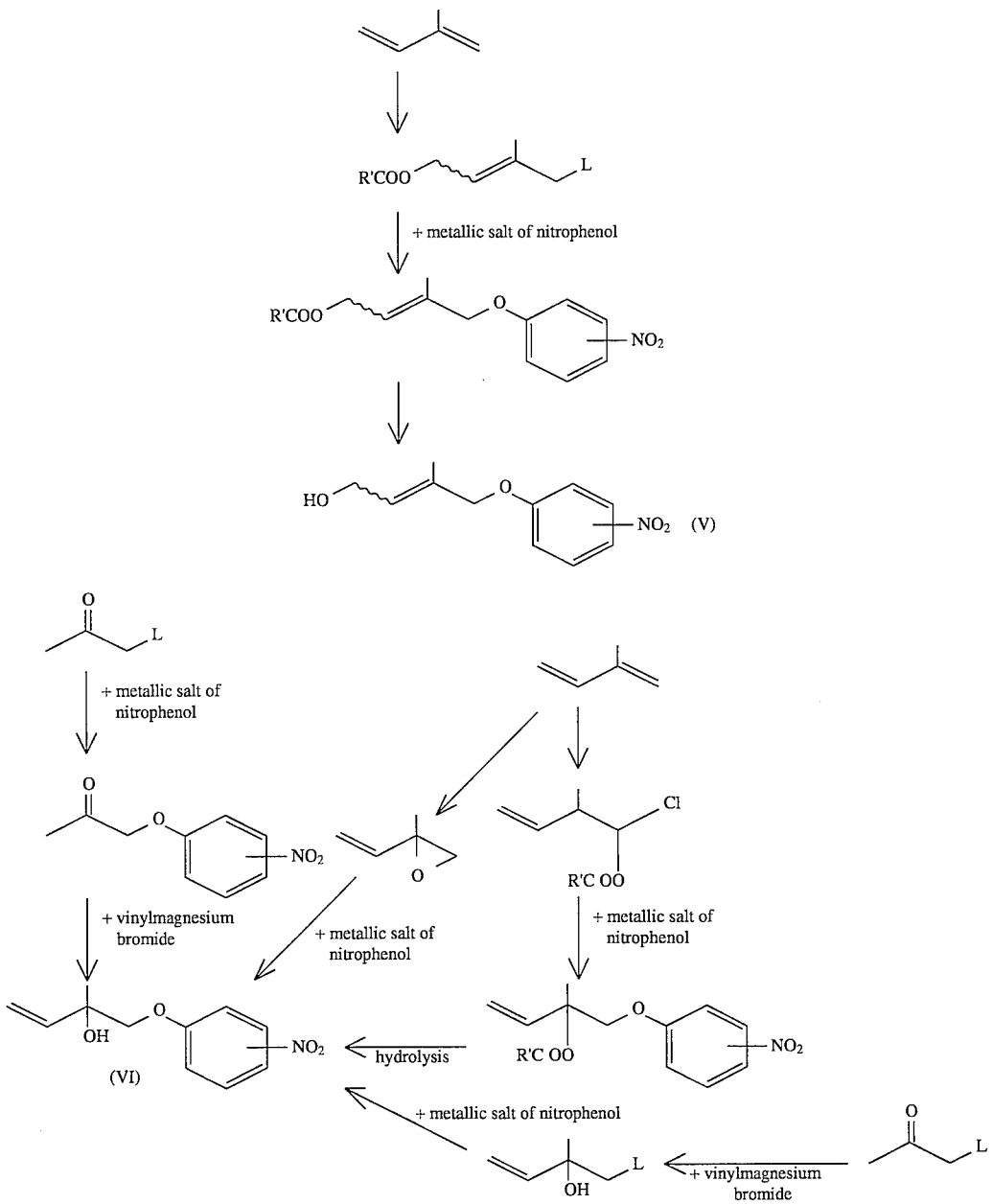

Now, the preparation process according to the present invention will be hereinafter described in detail.

Step 1

This step comprises reacting a trimethyl hydroquinone derivative (IV) with a primary allyl alcohol derivative (V) or tertiary allyl alcohol derivative (VI) to prepare a hydroquinone derivative (I) or acyl hydroquinone derivative (III). This reaction can be carried out in accordance with an usual Friedel-Crafts reaction method. Although a catalyst utilizable here is not limited, zinc chloride, aluminium chloride or a borone trifluoride-ether complex is preferred, and the addition of silica gel can improve a yield. In addition, a solvent is also not limited, and methylene chloride, dioxane, tetrahydrofuran, ethyl acetate, toluene, n-hexane, isopropyl ether or carbon disulfide is preferred.

Step 2

This step comprises oxidizing the hydroquinone derivative (I) to prepare a quinone derivative (II). In this step, the hydroquinone derivative (I) can be oxidized in the presence of manganese dioxide, ceric ammonium nitrate, chromic anhydride, nitric acid, air, lithium chloride and cupric chloride, by use of one or more selected from the group consisting of air, 2,3-dichloro-5,6-dicyano-1,4 -benzoquinone and chloranil. Among these oxidizing agents, air chlornil or ceric ammonium nitrate can be preferably used in the presence of manganese dioxide, lithium chloride and cupric chloride. This step can be carried out by a usual oxidizing method.

Step 3

This step comprises hydolyzing the acyl hydroquinone derivative (III) with a Claisen alkali to prepare the hydrolyzate (III'). This step can be carried out by a usual method. "Claisen alkali" means an alcohol solution of potassium hydroxide or sodium hydroxide, and a methanol solution of potassium hydroxide is more preferred. Although the concentration of said hydroxide is not limited, it is usually 10–60 wt %, and a 20–20% solution is preferably used. This reaction is preferably carried out at a lower temperature such as 10° C. or less.

Step 4

This step comprises oxidizing the hydroquinone, i.e. the hydrolyzate (III') obtained as the result of the step 3 to prepare a quinone derivative (II). It can be carried out in the same manner as the step 2.

The quinone derivative (II) obtained as the results of the step 2 or 4 can be purified by a usual method such as recrystallization, silica-gel column chromotography, distillation or HPLC.

In order to prepare a chroman derivative useful as pharmaceuticals, such as 5-[{4-[(3,4-dihydro-6-hydroxy- 2,5,7, 8-tetramethyl-2H-1-benzopyrane-2-yl)methoxy] phenyl}methyl]-2,4-thiazolidinedion (Code Name: CS-045), from the quinone derivative (II) according to the present invention, it can be converted to the object substance by deriving the same quinone derivative to 6-hydroxy-2-(4-nitrophenoxymethyl)-2,5,7,8-tetramethyl chroman-3-en in accordance with the process described in EP-543,346, and treating said tetramethylchroman-3-en by the process described in Japanese Patent Publication No. 31,079/90.

Next, preparation examples for preparing a starting material necessary for putting the present invention into practice will be described before Embodiments are mentioned.

PREPARATION EXAMPLE 1

Synthesis of-(4-bromo-3-methyl-2-butenyl) acetate

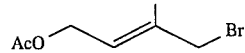

Into acetic acid (500 ml) were dissolved 85 g (1.25 mol) of isoprene. Under stirring at 15° C., 260 g (1.45 mol ) of N-bromosuccinimide were added therein dividedly four times little by little over two hours. Thereafter, the resulting mixture was stirred for additional two hours. The reaction liquid was added into ice water and extracted with ether. After the organic layer was washed with water, washed with a 5% aqueous solution of sodium hydrogencarbonate, washed with water and dried, the solvent was distilled off. The resulting residue was distilled under reduced pressure, whereby 115 g of the title compound were obtained. (Yield: 52.3%)

Boiling Point: 54°–60° C./0.3 mmHg [Literature Value: 57°–65° C./0.2 mmHg (Tetrahedron Letters, 239, 1976)], IR (cm$^{-1}$): 1720 (ester), $^1$H-NMR (90MHz, CDCl$_3$): δ (ppm) 1.84(3H,s), 2.05(3H, s), 3.93(2H,s), 4.55(2H,d,J=6 Hz), 5.66(1H,t,J=6 Hz).

PREPARATION EXAMPLE 2

Synthesis of [4-(p-nitrophenoxy)-3 -methyl-2-butenyl]acetate

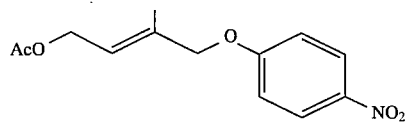

Into N,N-dimethyl formamide (which will be hereinafter called DMF, 300 ml) were suspended 22 g (0.55 mol) of 60%-oily sodium hydride. With stirring at 5° C. under ice cooling, a DMF (300 ml) solution containing 76 g (0.55 mol) of p-nitrophenol was added dropwise therein over three hours. Thereafter, the resulting mixture was stirred for further one hour. At room temperatures, a DMF (200 ml) solution containing 115 g (0.55 mol) of (4-bromo-3-methyl-2-butenyl) acetate was then added dropwise therein over three hours. Thereafter, the resulting mixture was stirred for additional two hours. The reaction liquid was added into water and extracted with ethyl acetate. After the organic layer was washed with water and dried, the solvent was distilled off. The resulting residue was purified by chromatography on a silica gel column (ethyl acetate: n-hexane system), whereby 120 g of the title compound were obtained in the form of a light-yellow oil. (Yield: 82.8%)

IR (cm$^{-1}$): 1720 (ester), 1530, 1350 (nitro), $^1$H-NMR (90MHz, CDCl$_3$): δ (ppm) 1.76(3H,s), 1.97(3H, s), 4.43(2H,s), 4.62(2H,d,J=7 Hz), 5.66(1H,t,J=7 Hz), 6.90 (2H,d,J=8 Hz), 8.11(2H,d,J=8 Hz).

PREPARATION EXAMPLE 3

Synthesis of 4-(p-nitrophenoxy)-3-methyl-2-butene-1-ol

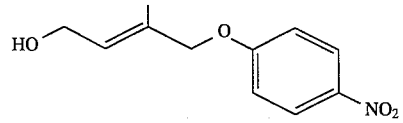

Into methanol (1,200 ml) and water (400 ml) were dissolved 120 g (0.25 mol) of [4-(p-nitrophenoxy)-3-methyl-2-butenyl]acetate. With stirring at room temperatures, 40 g (0.29 mol) of potassium carbonate were added therein, and stirred for one hour. The reaction liquid was added into water and extracted with ethyl acetate. After the organic layer was washed with water and dried, the solvent was distilled off, whereby 98.5 g of the title compound were obtained. (Yield: 98.5%)

Melting Point: 41°–43° C.

IR (cm$^{-1}$): 3200 (OH), 1535, 1350 (nitro), $^1$H-NMR (90 MHz, CDCl$_3$): δ (ppm) 1.74(3H,s), 2.25(1H,br), 4.20(2H,d,J=6 Hz), 4.45(2H,s), 5.73(1H,t,J=6 Hz), 6.90 (2H,d,J=8 Hz), 8.11(2H,d,J=8 Hz).

PREPARATION EXAMPLE 4

Synthesis of p-nitrophenoxy acetone

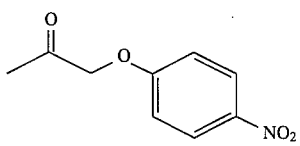

Into acetone (300 ml) were suspended 41.7 g (0.3 mol) of p-nitrophenol and 41.4 g (0.3 mol) of anhydrous potassium carbonate. Under stirring and reflux, 27.7 g (0.3 mol) of chloroacetone were added dropwise therein over five hours. After the resulting mixture was reacted for two hours as it was, it was cooled down, and the reaction liquid was dispersed into ice water (500 ml). After the extract obtained by extraction therefrom with ethyl acetate (500 ml) was washed with water and dried, the solvent was distilled off under reduced pressure. The thus-obtained light-yellow crystalline residue was recrystallized from ethyl acetate/n-hexane, whereby 48.1 g of the title compound were obtained. (Yield: 82.2%)

Melting Point: 77°–78° C.

IR (cm$^{-1}$): 1715 (C=O), 1510, 1320 (NO$_2$), $^1$H-NMR (4000 MHz, CDCl$_3$): δ (ppm) 2.25(3H,s), 4.66(2H,s), 6.92(2H,d,J=6 Hz), 8.17(2H,d,J=6 Hz), MS: m/e 195(M+).

PREPARATION EXAMPLE 5

Synthesis of 1-(p-nitrophenoxy)-2-methyl-3-butene-2-ol

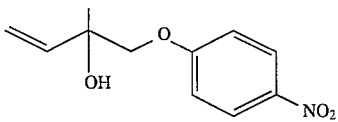

Into tetrahydrofuran (100 ml) were dissolved 19.5 g (0.1 mol) of p-nitrophenoxy acetone. With stirring under ice cooling and with keeping its internal temperature at 5°–10° C., 100 ml (0.1 mol) of a 1M-vinylmagnesium bromide. tetrahydrofuran solution were added dropwise therein over three hours. After the resulting mixture was continuously stirred for one hour as it was, the reaction liquid was dispersed into 5%-dilute hydrochloric acid (200 ml). After the extract obtained by extraction therefrom with ethyl acetate (200 ml) was washed with water and dried, the solvent was distilled off under reduced pressure. The thus-obtained yellowish brown and oily residue was purified by chromatography on a silica gel column (ethyl acetate/n-hexane system), whereby 12.5 g of the title compound were obtained in the form of a yellow oil. (Yield: 56%)

IR (cm$^{-1}$): 3200 (OH), 1520, 1345 (NO$_2$), $^1$H-NMR (4000 MHz, CDCl$_3$): δ (ppm) 1.40 (3H,s), 2.34 (1H,s), 3.92(2H,d,J=4 Hz), 5.22(1H,d,J=7 Hz), 5.40(1H,d, J=10 Hz), 6.00(1H,dd,J=7~10 Hz), 6.92(2H,d,J=4 Hz), 8.15(2H,d,J=4 Hz), MS: m/e 224 (MH$^+$).

PREPARATION EXAMPLE 6

Synthesis of (1-chloro-2-methyl-3-butene-2-yl) acetate

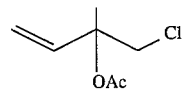

82 g (1.2 mol) of Isoprene and 360 g of glacial acetic acid were mixed. With stirring under ice cooling and with keeping an internal temperature at 10°–15° C., 108 g (1.0 mol) of t-butyl hypochlorite were added dropwise therein. The resulting mixture was continuously stirred as it was until the yellow color of said t-butyl hypochlorite disapperared from the reaction liquid. After water (500 ml) was added into the reaction liquid, it was extracted with ether (300 ml×2). After the organic layer was washed with an aqueous solution saturated with sodium hydrogencarbonate, and thereafter with water and dried, it was concentrated under reduced pressure, thereby obtaining an oily residue. This residue was distilled under reduced pressure, whereby 120 g of the title compound were obtained. (Yield: 43%)

IR (cm$^{-1}$): 1720 (COO), $^1$H-NMR (4000 MHz, CDCl$_3$): δ (ppm) 1.40(3H,s), 2.05(3H,s), 3.92(2H,s), 5.22(1H,[d,J=7 Hz), 5.40 (1H,d,J= 10 Hz), 6.00 (1H,dd,J=7~10 Hz), MS: m/e 224 (MH$^+$).

These measurement data were identified with the data as set forth in the literature [Journal of The Agricultural Chemical Society, 47 (12), 807–811, (1973).]

PREPARATION EXAMPLE 7

Synthesis of 1-(p-nitrophenoxy)-2-methyl-3-butene-2-ol

Into N,N-dimethyl formamide (200 ml) were suspended 11 g (0.27 mol) of 60%-sodium hydride. With stirring under ice cooling, an N,N-dimethyl formamide (150 ml) solution containing 38 g (0.27 mol) of p-nitrophenol was added dropwise therein over three hours. After the resulting solution was continuously stirred for further one hour as it was, the reaction liquid became a homogeneous yellow solution. The reaction liquid was returned to room temperatures, and an N,N-dimethylformamide (100 ml) solution containing 38 g (0.23 mol) of (1-chloro-2-methyl-3-butene-2-yl) acetate was added dropwise therein over three hours. The resulting mixture was stirred for additional one hour as it was. The reaction liquid was dispersed in water (1,000 ml), and 20 g of potassium carbonate were added therein, followed by stirring for one hour. After the extract obtained by extraction therefrom with ethyl acetate (500 ml) was washed with water and dried, it was concentrated under reduced pressure, thereby obtaining a yellowish brown and oily residue. This residue was purified by chromatography on a silica gel column (ethyl acetate:n-hexane system), whereby 36.5 g of the title compound were obtained. (Yield: 70.8%)

For concrete explanation of the present invention, Examples will be hereinafter described. Needless to say, the Present invention is not limited to these Examples.

EXAMPLE 1

Synthesis of 2-[4'-(p-nitrophenoxy)-3-methyl-2'-butenyl]-3,5,6-trimethyl-1,4-hydroquinone

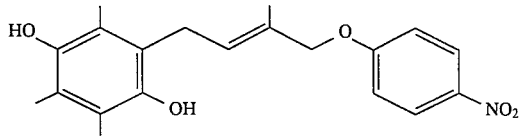

Into methylene chloride (50 ml) were suspended 3.1 g (0.02 mol) of 2,3,5-trimethyl-1,4-hydroquinone and 2.7 g (0.02 mol) of zinc chloride under an argon gas stream. With warming at 40° C. and suspending, a methylene chloride (20 ml) solution containing 4.46 g (0.02 mol) of 4-(p-nitrophenoxy)- 3-methyl-2-butene-1-ol was added dropwise therein over 30 minutes. Thereafter, the resulting mixture was continuously stirred for further three hours. The reaction liquid was poured into water and extracted with methylene chloride, and the extract was dried and the solvent was distilled off, thereby obtaining a raw product of the title compound. This raw product was purified by chromatography on a silica gel column (ethyl acetate: n-hexane system), whereby 3.7 g of the title compound were obtained in the form of white crystal. (Yield: 51.8%)

Melting point: 158°–160° C.

IR (cm$^{-1}$): 3450 (OH), 1530, 1325 (NO$_2$), $^1$H-NMR (90 MHz, CDCl$_3$): δ (ppm) 1.85(3H,s), 2.08(3H,s), 2.11(6H,s), 3.41(2H,d,J=6 Hz), 4.25(2H,br), 4.41(2H,s), 5.48(1H,t,J=6 Hz), 6.86(2H,d,J=7 Hz), 8.09(2H, d,J=7 Hz), MS: m/e 358 (MH$^+$).

EXAMPLE 2

Synthesis of 2-[4'-(p-nitrophenoxy)-3'-methyl-2'-butenyl]-3,5,6-trimethyl-1,2-hydroquinone Into a mixed liquid of toluene (40 ml) and n-hexane (20 ml) were suspended 9.1 g (0.06 mol) of 2,3,5-trimethyl-1,4-hydroquinone, 8.1 g (0.06 mol) of zinc chloride and 9.1 g of 200-mesh silica gel, followed by stirring at 40° C. for one hour under an argon gas stream. Into the resulting suspension, under stirring as it was, a toluene (30 ml) solution containing 17.6 g (0.06 mol) of 1-(p-nitrophenoxy)- 2-methyl-3-butene-2-ol (having a purity of 76%) was gradually added dropwise over eight hours. The resulting mixture was continuously stirred for further ten hours as it was. After the reaction liquid was cooled by ice, n-hexane (100 ml) was added thereto, and the reaction liquid was filtered, thereby obtaining a solid residue. This solid residue was washed with ethyl acetate (150 ml), and the filtrate was concentrated under reduced pressure, whereby 12.4 g of the title compound were obtained in the form of white cystal. (Yield: 57.9%)

EXAMPLE 3

Synthesis of 2-[4'-(p-nitrophenoxy)-3'-methyl-2'-butenyl]-3,5,6-trimeyl-1,4-benzoquinone

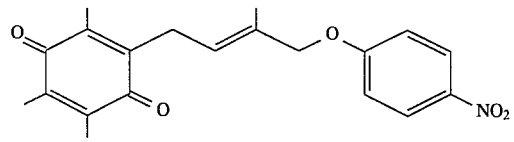

Into ethyl acetate (30 ml) were dissolved 3.6 g (0.01 mol) of 2-[4'-(p-Nitrophenoxy)-3'-methyl-2'-butenyl]-3,5,6 -trimethyl-1,4-hydroquinone. Under stirring at room temperatures, 4 g of manganese dioxide were added therein, followed by stirred for 30 minutes. The reaction liquid was filtered and the filtrate was concentrated, whereby 3.5 g of the title compound were obtained in the form of yellow crystal. (Yield: 98%)

Melting Pont: 79°–80° C.,

IR (cm$^{-1}$): 1660, 1635 (C=O), 1530, 1340 (NO$_2$), $^1$H-NMR (90 MHz, CDCl$_3$): δ (ppm) 1.73(3H,s), 1.90(6H,s), 1.93(3S,s), 3.21(2H,d,J=6 Hz), 4.38(2H,s), 5.35(1H,t,J=6 Hz), 6.94(2H,d,J=8 Hz), 8.05(2H,d,J=8 Hz).

EXAMPLE 4

Synthesis of 2-[4'-(p-nitrophenoxy)-3'-methyl-2'-butenyl]-3,5,6-trimethyl-1,4-benzoquinone Into a mixed solvent of toluene (60 ml) and ethanol (30 ml) were dissolved 10.7 g (0.03 mol) of 2-[4'-(p-nitrophenoxy)- 3'-methyl-2'-butenyl]-3,5,6-trimethyl-1,4 -hydroquinone. Into the resulting solution, an aqueous solution (30 ml) containing 0.5 g of anhydrous cupric chloride and 1.1 g of lithium chloride dissolved therein was further added. With blowing air at room temperatures, the resulting mixture was stirred for five hours. After the organic layer was separated therefrom, it was washed with water, dried and distilled under reduced pressure, whereby 10.2 g of the title compound were obtained in the form of yellow crystal. (Yield: 96.0%)

EXAMPLE 5

Synthesis of 2-[4'-(p-nitrophenoxy)-3'-methyl-2'-butenyl]-3,5,6-trimethyl-1,4-benzoquinone Into a mixed liquid of toluene (30 ml) and n-hexane (30 ml) were suspended 9.1 g (0.06 mol) of 2,3,5-trimethyl-1,4-hydroquinone, 5.6 g (0.04 mol) of zinc chloride and 9.1 g of 200-mesh silica gel, followed by stirring at 40° C. for one hour under an argon gas stream. Into the resulting suspension, with stirring as it was, a toluene (30 ml) solution containing 15.3 g (0.06 mol) of 1-(p-nitrophenoxy)- 2-methyl-3-butene-2-ol (having a purity of 87%) was gradually added dropwise over eight hours. The resulting mixture was continuously stirred for further seventeen hours as it was. After adding n-hexane (90 ml) into the reaction liquid, it was cooled by ice and stirred for two hours. Then, the reaction liquid was filtered, thereby obtaining a solid residue.

This residue was suspended in a mixed solvent of toluene (120 ml) and ethanol (50 ml). Into the resulting suspension, an aqueous solution (50 ml) containing 0.8 g of anhydrous cupric chloride and 2.0 g of lithium chloride dissolved therein was further added. With blowing air at room temperatures, the resulting solution was stirred for eight hours. After the organic layer was separated therefrom, washed with water, dried and distilled under reduced pressure, thereby obtaining a raw product of the title compound. This raw product was recrystallized from ethyl acetate/isopropyl ether, whereby 12.4 g of the title compound were obtained in the form of crystal. (Yield from 2,3,5-trimethyl-1,4-hydroquinone: 58.2%).

EXAMPLE 6

Synthesis of
{2-[4'-(p-nitrophenoxy)-3'-methyl-2'-butenyl]-3,5,6-trimethyl-1,4-hydroquinone-4-yl}acetate

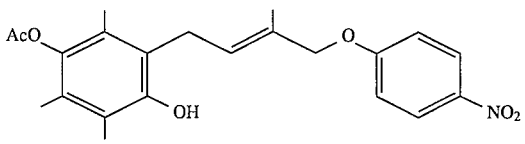

Into methylene chloride (100 ml) were suspended 19.4 g (0.1 mol) of (2,3,5-trimethyl-1,4-hydroquinone-4-yl) acetate and 13.6 g (0.1 mmol) of zinc chloride under an argon gas stream. With warming at 40° C. and stirring, a methylene chloride (50 ml) solution containing 22.3 g (0.1 mol) of 4-(p-nitrophenoxy)-3-methyl-2-butene-1-ol was added dropwise therein over two hours. Thereafter, the resulting mixture was continuously stirred for further five hours. The reaction liquid was poured into water and extracted with methylene chloride. The extract was dried and the solvent was distilled off, thereby obtaining a raw product of the title compound. This raw product was purified by chromatography on a silica gel column (ethyl acetate:n-hexane system), whereby 29.4 g of the title compound were obtained in the form of light-yellow crystal. (Yield: 74.6%)

Melting Pont: 133°–132° C.

IR (cm$^{-1}$): 3270 (OH), 1730 (COO), 1520, 1340 (NO$_2$), $^1$H-NMR (90 MHz, CDCl$_3$): δ (ppm) 1.84(3H,s), 2.02(6H,s), 2.06(3H,s), 2.18(3H,s), 3.42(2H,d,J=6 Hz), 4.44(2H,s), 4.81(1H,s), 5.52(1H,t,J=6 Hz), 6.95(2H,d,J=8 Hz), 8.15 (2H,d,J=8 Hz), MS: m/e 400(MH$^+$).

EXAMPLE 7

Synthesis of
2-[4'-(p-nitrophenoxy)-3'-methyl-2'-butenyl]-3,5,6-trimethyl-1,4-benzoquinone Into acetonitrile (150 ml) and water (30 ml) were dissolved 12 g (0.03 mol) of {2-[2'-(p-nitrophenoxy)-3'-methyl-2'-butenyl]-3,5,6-trimethyl-1,4-hydroquinone-4-yl}acetate. Under stirring at room temperatures, 17 g (0.03 mol) of ceric ammonium nitrate were added dividedly thrice therein. Thereafter, the resulting mixture was continuously stirred for further 30 minutes. The reaction liquid was poured into water and extracted with toluene, and the extract was dried and the solvent was distilled off, whereby 9.8 g of the title compound were obtained in the form of yellow crystal. (Yield: 92.4%).

This product was identified with the title compound obtained in Example 3, on TLC, HPLC and capillary GC.

EXAMPLE 8

Synthesis of
2-[4'-(p-nitrophenoxy)-3'-methyl-2'-butenyl]-3,5,6-trimethyl-1,4-benzoquinone Into acetone (50 ml) were dissolved 5 g (12.5 mmol) of {2-[4'-(p-nitrophenoxy)-3'-methyl-2'-butenyl]-3,5,6-trimethyl-1,4-hydroquinone-4-yl}acetate. Under stirring at 5° C., a 30%-potassium hydroxide/methanol solution (5 ml) was added dropwise therein over 30 minutes. The reaction liquid was poured into ice water and extracted with ethyl acetate. Into the extract were added 4 g of manganese dioxide, followed by stirring at room temperatures for 30 minutes. The reaction liquid was filtered and the filtrate was concentrated, thereby obtaining a raw product of the title compound. This raw product was purified by chromatography on a silica gel column (n-hexane:toluene system), whereby 3.8 g of the title compound were obtained in the form of yellow crystal. (Yield: 85.8%).

The product was identified with the title compound obtained in Example 3, on TLC, HPLC and capillary GC.

Melting Point: 79°–80° C.

EXAMPLE 9

Synthesis of
{2-[4'-(p-nitrophenoxy)-3'-methyl-2'-butenyl]-3,5,6-trimethyl-1,4-hydroquinone-4-yl}benzoate

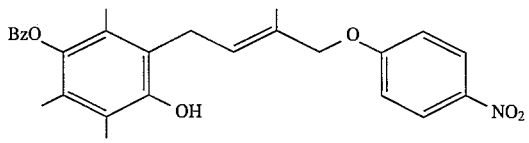

Into ethyl acetate (50 ml) were added 5.2 g (0.02 mol) of (2,3,5-trimethyl-1,4-hydroquinone-2-yl) benzoate and 2.7 g (0.02 mmol) of zinc chloride under an argon gas stream. With warming at 40° C. and stirring, a toluene (20 ml) solution containing 4.46 g (0.02 mol) of 4-(p-nitrophenoxy)-3-methyl- 2-butene-1-ol was added dropwise therein over one hour. Thereafter, the resulting mixture was continuously stirred for further three hours. The reaction liquid was poured into water and extracted with toluene, and the extract was dried and the solvent was distilled off, thereby obtaining a raw product of the title copound. This raw product was purified chromatography on a silica gel column (ethyl acetate:n-hexane system ), whereby 6.7 g of the title compound were obtained in the form of light-yellow crystal. (Yield: 72.6%).

Melting Point: 189°–192° C.

IR (cm$^{-1}$): 3460 (OH), 1740 (COO), 1520, 1320 (NO$_2$), $^1$H-NMR (90 MHz, CDCl$_3$): δ (ppm) 1.82(3H,s), 2.02(6H,s), 2.06(3H,s), 3.40(2H,d,J=6 Hz), 4.42(2H,s), 4.90(1H,s), 5.54(1H,t,J=6 Hz), 6.95(2H,d,J=8 Hz), 7.48(2H, t,J=6 Hz), 7.58(1H,t,J=6 Hz), 8.15(2H,d,J=8 Hz), 8.22(2H, d,J=6 Hz), MS: m/e 462(MH$^+$).

EXAMPLE 10

Synthesis of 2-[4'-(p-nitrophenoxy)-3-methyl-2'-butenyl]-3,5,6-trimethyl-1,4-benzoquinone Into acetone (50 ml) were dissolved 4.6 g (0.01 mol) of {2-[4'-(p-nitrophenoxy)-3'-methyl-2'-butenyl]-3,5,6-trimethyl- 1,4-hydroquinone-4-yl}benzoate. Under stirring at 5° C., a 30%-potassium hydroxide/methanol solution (4 ml) was added dropwise therein over 30 minutes. The reaction liquid was poured into ice water and extracted with ethyl acetate. Into the extract were added 4 g of manganese dioxide, followed by stirring at room temperatures for 30 minutes. The reaction liquid was filtered and the filtrate was concentrated, thereby obtaining a raw product of the title compound. This raw product was purified by chromatography on a silica gel column (n-hexane:toluene system), whereby 2.8 g of the title compound were obtained in the form of yellow crystal. (Yield: 78.8%).

The product was identified with the title compound obtained in Example 3, on TLC, HPLC and capillary GC.

What is claimed is:

1. A process for preparing a quinone derivative (II), represented by the following formula:

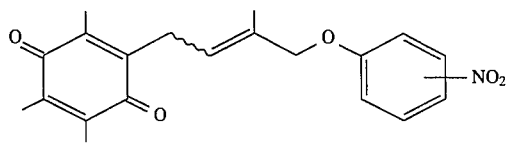
(II)

which comprises oxidizing a hydroquinone derivative (I) represented by the following formula:

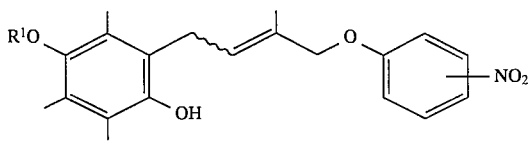
(I)

wherein $R^1$ represents a hydrogen atom, with one or more oxidizing agents selected from the group consisting of:

i) 2,3-dichloro-5,6-dicyano1,4-benzoquinone;
ii) chloranil in the presence of manganese dioxide;
iii) ceric ammonium nitrate;
iv) chromic anhydride;
v) nitric acid; and
vi) a mixture of air, lithium chloride and cupric chloride; thereby preparing the quinone derivative (II).

2. A process for preparing a quinone derivative (II), represented by the following formula:

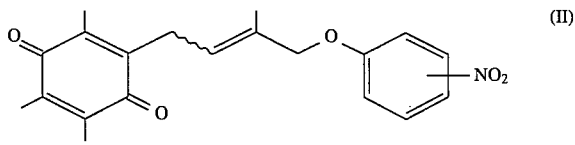
(II)

which comprises hydrolyzing with a Claisen alkali, an acyl hydroquinone derivative (III) represented by the following formula:

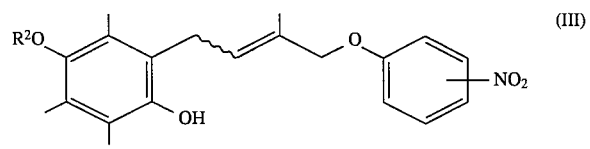
(III)

wherein $R^2$ represents an aliphatic acyl group or aromatic acyl group, followed by oxidizing the resulting hydrolyzate (III') represented by the following formula:

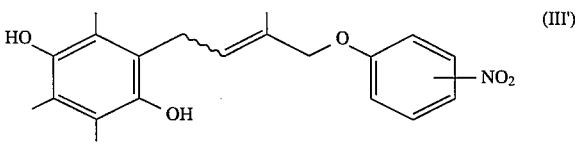
(III')

with one or more oxidizing agents selected from the group consisting of:

i) 2,3-dichloro-5,6-dicyano-1,4-benzoquinone;
ii) chloranil in the presence of manganese dioxide;
iii) ceric ammonium nitrate;
iv) chromic anhydride;
v) nitric acid; and
vi) a mixture of air, lithium chloride and cupric chloride; thereby preparing the quinone derivative (II).

* * * * *